United States Patent
Nakanishi et al.

(10) Patent No.: US 6,759,031 B2
(45) Date of Patent: Jul. 6, 2004

(54) SILICONE COMPOUND, AND A MAKEUP CONTAINING THIS COMPOUND

(75) Inventors: Tetsuo Nakanishi, Gunma-ken (JP); Ichiro Ono, Gunma-ken (JP); Toru Shimizu, Tokyo (JP)

(73) Assignee: Shi-Etsu Chemical Co., Ltd., Tokyo (JP)

( * ) Notice: Subject to any disclaimer, the term of this patent is extended or adjusted under 35 U.S.C. 154(b) by 92 days.

(21) Appl. No.: 10/136,310

(22) Filed: May 2, 2002

(65) Prior Publication Data

US 2002/0159964 A1 Oct. 31, 2002

Related U.S. Application Data

(62) Division of application No. 09/772,963, filed on Jan. 31, 2001, now Pat. No. 6,479,686.

(30) Foreign Application Priority Data

Feb. 1, 2000 (JP) .......................................... 2000/23869

(51) Int. Cl.$^7$ ................................................. A61K 7/42
(52) U.S. Cl. .............................. 424/59; 424/63; 424/65; 424/70.1; 424/70.12; 424/401
(58) Field of Search .............................. 424/59, 63, 65, 424/70.1, 70.12, 401

(56) References Cited

U.S. PATENT DOCUMENTS 3,502,769 A    3/1970   Fukuhara 4,336,246 A    6/1982   Leon-Pekarek
5,505,937 A    4/1996   McCulley et al.

FOREIGN PATENT DOCUMENTS

GB    2124081    2/1984

*Primary Examiner*—Samuel Barts
(74) *Attorney, Agent, or Firm*—Millen, White, Zelano & Branigan, P.C.

(57) ABSTRACT

This invention relates to a makeup containing a specific modified silicone obtained by an economical manufacturing method not requiring an esterification catalyst, having a high reaction rate and therefore leaving little unreacted material, and in particular relates to a makeup with good skin adhesion, good retention and excellent emulsion stability.

A silicone compound represented by the general formula (1):

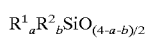

$$R^1_a R^2_b SiO_{(4-a-b)/2}$$

(in the formula, $R^1$ is at least one substituent group having 1–30 carbon atoms, chosen from alkyaryl, aralkyl, fluorine-substituted alkyl or organopolysiloxanylsilyl, $R^2$ is a carboxylate residue represented by the following general formula (2):

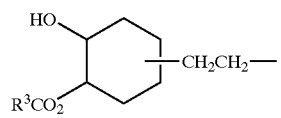

$R^3$ is a saturated or unsaturated hydrocarbon group having 2–30 carbon atoms, a is 1.0–2.5, and b is 0.001–1.5.

31 Claims, No Drawings

SILICONE COMPOUND, AND A MAKEUP CONTAINING THIS COMPOUND

This application is a division of Ser. No. 09/772,963 filed Jan. 31, 2001 now U.S. Pat. No. 6,479,686.

FIELD OF THE INVENTION

This invention relates to a makeup containing a specific modified silicone obtained by an economical manufacturing method not requiring an esterification catalyst, having a high reaction rate and therefore leaving little unreacted material, and in particular to a makeup with good skin adhesion, good retention and excellent emulsion stability.

BACKGROUND OF THE INVENTION

In general, male secretions such as sweat, tears and sebum, lead to messy makeup, and sebum secreted from the skin becomes mixed with the oil in which the makeup is blended. This is a major reason why too much wetting of the powder in the makeup leads to messy makeup. To reduce the oil in makeup remaining on the skin, it has been attempted to use volatile oils, such as octamethylcylotetrasiloxane and decamethylcyclopentasiloxane, as part of the blended oils.

Friction and water, etc., are external factors which impair makeup retention. To improve the poor makeup retention which occurs due to water-soluble substances, such as sweat and tears, loss of water-soluble components and sebum, etc., in the skin is prevented, and the protective effect of the skin is maintained, by blending with silicone oils which increase water repellent properties.

Since they have the characteristic features of light feel, outstanding water-repellent properties and high safety, silicone oils such as dimethylpolysiloxane for example are being used profusely in makeup oils in recent years.

Although dimethylpolysiloxanes have excellent properties as oils for use in cosmetics, it cannot be said that significant improvements had been made regarding enhanced water repellency and adhesion to the skin when they were used in makeup.

In skin care products also, oils were desired with a light feel, water repellent properties and ease of use which would impart a feeling of adhesion to the skin.

In the prior art, resins such as rosin or rosin esters purified from well-known resins for example are occasionally used to improve the adhesion in cosmetics, but they have poor solubility in silicone oils and it was difficult to blend them with makeup using silicone as a foundation material.

For example, in U.S. Pat. Nos. 2,610,496 (Koho), 2,665,799 (Koho) and 2,750,748 (Koho), a makeup is disclosed using the silicone derivative of a hydrate of abietic acid which is contained in rosin to the extent of about 60%. The tetrahydroabietic acid-modified silicone in these patents is synthesized by:

1) a reaction between an alcohol-denatured silicone and tetrahydroabietic acid or tetrahydroabietic acid chloride, or
2) an addition reaction between an ester of tetrahydroabietic acid, an allylpolyoxyethylene alcohol and hydrogen polysiloxane, but the step for synthesizing tetrahydroabietic acid chloride, and the reactions between tetrahydroabietic acid and alcohol-denatured silicone or allylpolyoxyethylene alcohol are all reactions performed under acid conditions, and when resin acids are used containing a large amount of an unsaturated tricyclic diterpene carboxylic acid such as abietic acid, polymerization may occur giving an extreme coloration, and resulting in an alcohol insoluble substance. Therefore, when using this type of reaction, it was necessary to first perform a hydrogen addition reaction to give a saturated resin acid as described in the above patents. Further, when an acid catalyst was used, subsequent steps such as rinsing with water were necessary after the reaction, so the method of synthesis could not be described as economical. Therefore, a method was desired which could simply and cheaply synthesize abietic acid-modified silicones by direct reaction of rosin, which is an unsaturated tricyclic diterpene carboxylic acid, by a reaction not using an acid catalyst.

Problems which this Invention Attempts to Solve

It is therefore an object of this invention to provide a method of synthesizing a silicone compound more cheaply and economically than in the prior art by the heat addition reaction of an unsaturated or unsaturated carboxylic acid having 2–30 carbon atoms, and an alicyclic epoxy compound. The modified silicone obtained by this method does not give rise to alcohol insoluble substances, produces little coloration, and does not use an acid catalyst. Further, makeup which uses this modified silicone are extremely water repellent and have excellent adhesion, while at the same time, it is soluble in volatile oils such as octamethylcylotetrasiloxane and decamethylcyclopentasiloxane, and is therefore easy to use as a cosmetic oil. Moreover, such makeup has a lighter feel than makeup using prior art resins. When this silicone compound is used as an oil in emulsion systems, it has excellent miscibility with oils used in ordinary cosmetics such as silicone oils, ester oils and triglycerides.

Means for Solving the Problems

The main object of this invention is a silicone compound represented by the general formula (1):

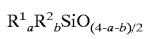

$R^1{}_a R^2{}_b SiO_{(4-a-b)/2}$ (in the formula, $R^1$ is at least one substituent group having 1–30 carbon atoms chosen from alkyl, aryl, aralkyl, fluorine-substituted alkyl or organopolysiloxanylsilyl, $R^2$ is a carboxylate residue represented by the following general formula (2),

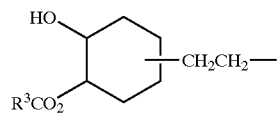

$R^3$ is a saturated or unsaturated hydrocarbon group having 2–30 carbon atoms, a is 1.0–2.5, and b is 0.001–1.5.

Another object of this invention is the above-mentioned silicone compound wherein $R^3$ is a tricyclic diterpene carboxylic acid. Yet another object of this invention is the above-mentioned silicone compound wherein at least part of $R^1$ is represented by the following general formula (3)

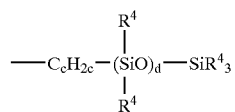

$$—C_cH_{2c}—(SiO)_d—SiR^4{}_3$$
with $R^4$ substituents (in the formula, $R^4$ may respectively be identical or different, and is at least one substituent group having 1–30 carbon atoms chosen from alkyl, aryl, aralkyl, fluorine substituted alkyl or hydroxyl, c is 1–5, and d is 0–500).

Another object of this invention is a makeup containing 0.1–99.5 weight % of the aforesaid silicone compound and 0.5–99.9 weight % of oil, and skin care products, hairdressing products, antiperspirant, makeup products, and ultraviolet defense products which partly contain this makeup material. It may also be in the form of a liquid, emulsion, cream, solid, paste, gel, powder, laminate, mousse or spray.

Yet another object of this invention is a method to synthesize any of the aforesaid silicone compounds by synthesizing an alicyclic epoxy-modified silicone by an addition reaction of a main chain siloxane such as an organohydrogenpolysiloxane to a vinyl alicyclic epoxide, and reacting these with a saturated or unsaturated carboxylic acid.

Embodiments

The silicone compound a) of this invention may be represented by the general formula (1).

In the formula, a is 1.0–2.5 but preferably 1.2–2.3, and b is 0.001–1.5 but preferably 0.05–1.0. $R^1$ is at least one substituent group having 1–30 carbon atoms, chosen from alky, aryl, aralkyl, fluorine-substituted alkyl or organopolysiloxanylsilyl alkyl.

$R^1$ may be an alkyl group such as methyl, ethyl, propyl, butyl, pentyl, hexyl, heptyl, octyl, nonyl or decyl; a cycloalkyl group such as cyclopentyl or cyclohexyl; an aryl group such as phenyl or tolyl; an aralkyl group such as benzyl or phenetyl; an alcohol residue such as olioxy or alioxy; a fluorinated alkyl group such as trifluoropropyl or heptadecafluorodecyl, and organopolysiloxanylsilyl alkyl represented by the following general formula (3).

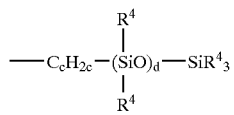

It is preferable that at least about 80% of $R^1$ are methyl groups. Moreover, it is preferable that at least part of $R^1$ is the organopolysiloxanylsilyl alkyl group represented by the above-mentioned general formula (3). In the above formula (3), $R^4$ may respectively be identical or different, and is at least one substituent group having 1–30 carbon atoms chosen from alkyl, aryl, aralkyl, fluorine-substituted alkyl or hydroxyl, and c is 1–5. In particular, when synthesizing this substituent from the reaction of a vinyl group and a SiH group, c is 2, and d is 0–500 but preferably 1–100.

When d is larger than 500, problems such as poor reactivity of the main chain may arise.

The silicone compound a) represented by the general formula (1) is synthesized by an equilibrium reaction using an acid or alkali catalyst according to standard methods. The branch silicone unit in this silicone compound is introduced by using a trialkoxymethylsilane, trihydroxymethylsilane, tris(trimethylsiloxy) methylsilane and their straight chain or cyclic polymers for the equilibrium reaction, or branched by performing a ring opening polymerization with a living polymerization catalyst using a silanol-denatured silicone.

The silicone which is branched by the organopolyxsiloxanylalkyl group shown by the general formula (3) can be synthesized by an addition reaction of an organohydrogen polysiloxane to a single-terminated vinyl denatured organopolysiloxane or vinyl denaturated organosilane represented by the following general formula (4).

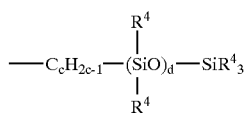

$R^2$ is a carboxylate residue represented by the following general formula (2).

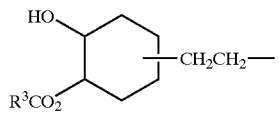

In the formula, $R^3$ is a saturated or unsaturated hydrocarbon group having 2–30 carbon atoms, preferably a resin acid residue such as acetic acid, butyric acid, capric acid, lauric acid, myristic acid, palmitic acid, stearic acid, behenic acid, melissic acid, palmitoleic acid, oleic acid, linolic acid, linolenic acid, arachidonic acid, erucic acid, 2-ethyl hexanoic acid, 2-hexyl decanoic acid, 2-heptyl undecanoic acid, 5,7,7-trimethyl-2-(1,3,3-trimethylbutyl)octanoic acid, methyl branched isostearic acid, cyclopentane carboxylic acid, cyclohexane carboxylic acid, cholic acid, deoxycholic acid, glycyl lysine acid, benzoic acid, naphthoic acid, undecylenic acid or a tricyclic diterpene carboxylic acid. Of these, resin acid residues such as tricyclic diterpene carboxylic acid, undecylenic acid which is a solid at ordinary temperature, stearic acid or erucic acid are to be preferred, and resin acid residues of tricyclic diterpene carboxylic acids are particularly to be preferred. As the resin acid residue of a tricyclic diterpene carboxylic acid, the resin acid residue of rosin or hydrated rosin is preferable. It may also be at least one carboxylic acid residue chosen from abietic acid, neoabietic acid, dihydroabietic acid, d-pimaric acid, iso d-pimaric acid, dihydroabietic acid, levopimaric acid, palustric acid, dextropimaric acid, sandarachpimaric acid, and their hydrates.

When the above makeup is used, there is no particular limitation on the weight average molecular weight of the aforesaid silicone compound a) (formula 1), but 500–200000 and especially 1000–100000 are to be preferred.

The silicone compound a) of this invention may be synthesized by carrying out an addition reaction of a main chain siloxane which is an organohydrogen polysiloxane represented by the following general formula (5):

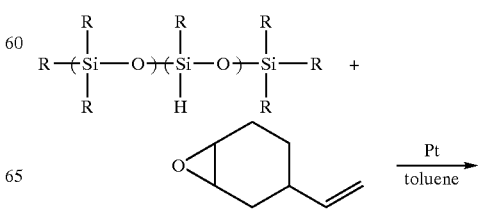

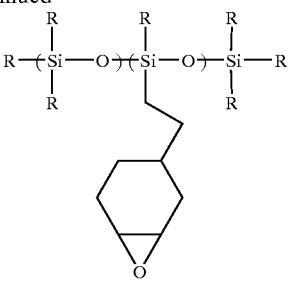

and a vinyl carboxylate to synthesize an alicyclic epoxy-modified silicone, and reacting this with saturated or unsaturated carboxylic acids, especially tricyclic diterpene carboxylic acid (abbreviated as X—COOH in the following reaction equation) according to the following reaction equation (6).

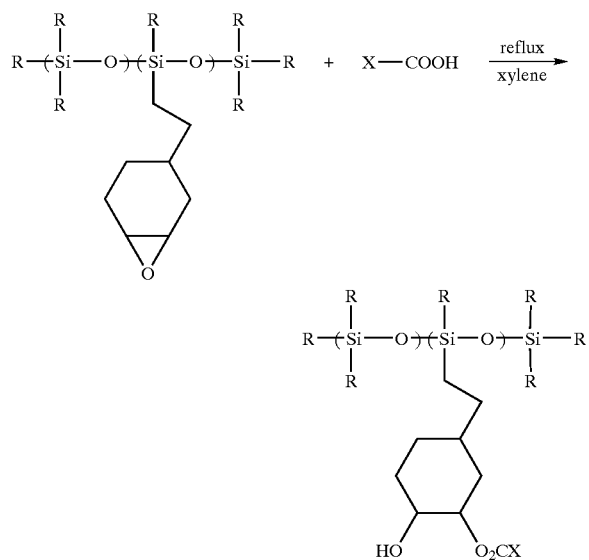

As the resin acid residue of a tricyclic diterpene carboxylic acid, the resin acid residue of rosin or hydrated rosin is preferable. It may also be at least one carboxylic acid residue chosen from abietic acid, neoabietic acid, dihydroabietic acid, d-pimaric acid, iso d-pimaric acid, dihydroabietic acid, levopimaric acid, palustric acid, dextropimaric acid, sandarachpimaric acid, and their hydrates.

The addition reaction of the hydrogen silicone compound to the single-terminal vinyl silicone compound or vinyl alicyclic epoxide may easily be carried out in the presence of a platinum catalyst or rhodium catalyst. Moreover, the reaction of the alicyclic epoxy-denatured silicone and carboxylic acid does not require a catalyst, and the reaction can be carried out simply by heating.

In another method, a vinyl alicyclic epoxide is first reacted with a tricyclic diterpene carboxylic acid, and an addition reaction with a hydrogen silicone compound may then be performed to obtain the product.

As these reactions do not use an acid catalyst, polymerization with saturated or unsaturated carboxylic acids, and particularly with tricyclic diterpene carboxylic acids, does not occur.

Here, the organohydrogen polysiloxane may be straight chain or cyclic, and a branched compound as in general formula (3) is also suitable. The mixing ratio of this organohydrogen polysiloxane and vinyl alicyclic epoxide is 0.5–1.5, and preferably 0.8–1.2, expressed as the mole ratio of terminal unsaturated groups to SiH groups.

The above-mentioned addition reaction is preferably performed in the presence of a platinum catalyst or a rhodium catalyst, suitable examples being chloroplatinic acid, alcohol-denatured chloroplatinic acid and chloroplatinic acid-vinyl siloxane complex, etc. The catalyst usage amount can be taken as the catalyst amount, which in terms of platinum or rhodium amount is 50 ppm or less, but more preferably 20 ppm or less. The above-mentioned addition reaction may be performed in an organic solvent if necessary. Examples of this organic solvent are aliphatic alcohols such as methanol, ethanol, 2-propanol, and butanol, aromatic hydrocarbons such as toluene and xylene, aliphatic or aromatic hydrocarbons such as n-pentane, n-hexane and cyclohexane, or halogenated hydrocarbons such as dichloromethane, chloroform and carbon tetrachloride.

The conditions of the above-mentioned addition reaction are not limited, but the reaction may conveniently be carried out under reflux for 1 to 10 hours.

The aforesaid reaction of the epoxy group and carboxylic acid is completed simply by heating at 60–200° C. in an organic solvent. Although an acid catalyst can also be used as a catalyst as it promotes the reaction, a catalyst is not required if an alicyclic epoxy group is used as in this invention. As organic solvents, aromatic hydrocarbons such as toluene and xylene which have a high boiling point may be given particular mention. This reaction may conveniently be carried out under reflux for 1 to 20 hours.

The content of the silicone compound a) of this invention is 0.1–99.5 weight %, but preferably 0.1–60 weight %. When this content is less than 0.1 weight % adhesion properties are insufficient, and if it exceeds 60 weight %. the desired makeup may not be obtained.

The following are examples of the oil b) which is a compositional component of this invention.

Examples of natural animal and vegetable fats and oils, and semi-synthetic fats and oils, include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, bees wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil. Additionally, the term "POE" as used herein stands for polyoxyethylene.

Examples of hydrocarbon oils include ozokerite, squalane, squalene, ceresine, paraffin, paraffin wax, liquid paraffin, pristane, polyisobutylene, microcrystalline wax and Vaseline; and those of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oils include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester, diisostearyl malic acid, dextrin palmitic acid ester, dextrin stearic acid ester, dextrin 2-ethylhexanic acid palmitic acid ester, cane sugar palmitic acid ester, cane sugar stearic acid ester, monobenzylidene sorbitol and dibenzylidene sorbitol.

Examples of glyceride oils include acetoglyceride, diisooctanoic acid glycride, triisostearic acid glyceride, triisopalmitic acid glyceride, tri-2-ethylhexanoic acid glyceride, monostearic acid glyceride, di-2-heptylundecanoic acid glyceride and trimyristic acid glyceride.

As examples of silicone oils, mention may be made of higher alkoxy-modified silicones such as dimethylpolysiloxane, methylphenyl-polysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane and stearoxysilicone, higher fatty acid-modified silicones, fluorine-modified silicones, amino-modified silicones, alkyl-modified silicones, higher fatty acid ester-modified silicones, silicone resins and silicone rubbers.

As examples of fluorine-containing oils, mention may be made of perfluoropolyether, perfluorodecalin and perfluorooctane.

One of more of these may be used as necessary.

It is preferable that these oils are liquid at ordinary temperature, more preferable that they are organic powders having a silicone resin and/or silicone elastomer skeleton with a structural repeating unit of —[O—Si—]n—, and still more preferable that these powders partially have at least a fluorine group or an amino group.

The content of the oil b) in the makeup of this invention is 0.5–99.9 weight %, preferably 0.5–95.0 weight %, and more preferably 1.0–50.0 weight %. If this content is less than 0.5 weight %, the effect of the oil cannot be obtained, and if it exceeds 95.0 weight %, the effect of the silicone compound a) of this invention (formula 1) may diminish.

Examples of compounds having an alcoholic hydroxyl group in the molecular structure c) of this invention are ethanol, propanol, ethylene glycol, ethylene glycol monoalkylether, diethylene glycol monoethylether, polyethylene glycol, propylene glycol, dipropylene glycol, 1,3-dibutylene glycol, glycerine, diglycerine, polyglycerine, pentaerythyrtol, cane sugar, lactose, xylitol, sorbitol, mannitol, maltitol, carrageenan, agar, agar gum, dextrin, traganto gum, locust bean gum, polyvinyl alcohol, polyoxyethylene polymers, polyoxyethylene polyoxypropylene copolymers, hyarulonic acid, chondroitin sulfate, chitin and chitosan. One or more of these may be used as necessary, but compounds which can dissolve the silicone compound a) of this invention (formula 1) are preferred.

It is preferred that the compound having an alcoholic hydroxyl group is a water-soluble, monohydric or polyhydric alcohol, or a water-soluble polymer.

The content of the compound c) containing alcoholic hydroxyl groups in the makeup of this invention is 0.5–50.0 weight %. If it is less than 0.5 weight %, moisturizing properties, antimicrobial properties and antibiological properties are insufficient, so it is preferably 0.5–50.0 weight %. If it exceeds 50.0 weight %, tackiness increases which is undesirable for a makeup material.

The makeup of this invention may also contain d) water as a compositional component. The water content in the makeup of this invention is 0–99.0 weight %, the blending proportion being increased or decreased according to the form of the makeup.

An excellent makeup according to this invention may be obtained from a) the silicone compound of this invention, b) an oil, c) a compound containing alcoholic hydroxyl groups and d) water, but e) powders and/or colorants, f) surfactants, g) cross-linked organopolysiloxanes and h) silicone resins, such as acryl/silicone graft or block copolymer, and silicone lattice compounds, etc., may also be added if necessary.

e) Powders and/or Colorants

Examples of a usable inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxie, boron nitride and silica.

Examples of a usable organic powder include polyamide powder, polyester powder, polyethylene powder, polypropylene powder, polystyrene powder, polyurethane powder, benzoguanamine powder, polymethylbenzoguanamine powder, polytetrafluoroethylene powder, polymethylmethacrylate powder, cellulose powder, silk powder, nylon powder such as 12-nylon powder or 6-nylon powder, silicone powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder, polycarbonate resin powder, microcrystalline fiber powder, starch powder and lauroyl lysine powder.

Examples of a usable surfactant metal salt powder (metal soap powder) include powders of zinc stearate, aluminum stearate, calcium stearate, magnesium stearate, zinc myristate, magnesium myristate, zinc cetylphosphate, calcium cetylphosphate and zinc sodium cetylphosphate.

Examples of a usable colored pigment include inorganic red pigments, such as iron oxide, iron hydroxide and iron titanate; inorganic brown pigments, such as gamma-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments as recited above.

Examples of a usable pearl pigment include titanium oxide-coated mica, bismuth oxychloride, titanium oxide-coated bismuth oxychloride, titanium oxide-coated talc, fish scales, and titanium oxide-coated colored mica; and examples of a usable metallic powder pigment include aluminum powder, copper powder and stainless powder.

Examples of a usable tar pigment include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207 (according to the pigment nomenclature method in JIS); and examples of a usable natural pigment include powders of carminic acid, laccaic acid, carthamin, bradilin and crocin.

The present silicone compounds are applicable to surface treatment of any powders so far as the powders can be used in general cosmetic materials, irrespective of their shape (whether it is spherical, acicular or tabular), their size (whether it is fume, fine grain or pigment), and their structure (whether it is porous or nonporous). It is preferred that part or all of the e) powder and/or colorant is an organic powder having a silicone resin and/or silicone elastomer skeleton with a structural repeating unit of —[O—Si—]n-. These powders may also be complexed and/or surface-treated with an oil, silicone or fluoride compound.

Furthermore, the present cosmetic materials can contain one or more surfactants, if desired.

Examples of a usable anionic surfactant include saturated or unsaturated fatty acid soaps such as sodium stearate or triethanolamine palmitate; alkyl ether carboxylic acids and salts thereof; salts of amino acid-fatty acid condensates; amido ether carboxylic acid salts; alpha-sulfo fatty acid esters, alpha-acyl sulfonic acid; alkylsulfonic acids; alkene-sulfonic acids; sulfonated fatty acid esters; sulfonated fatty acid amides; sulfonates of alkyl sulfonic acid salts and their formaldehyde condensates; alkyl sulfonic acid ester salts; secondary alcohol sulfates; alkyl and aryl ether sulfates; fatty acid ether sulfates, fatty acid alkylolamide sulfates; sulfate esters such as Turkey red oil; alkyl phosphates; alkenyl phosphates; ether phosphates; alkyl aryl ether phosphates; alkylamide phosphates; and active agents of N-acylamino acid type.

Examples of a usable cationic surfactant include amine salts, such as alkylamine salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopoly-siloxanes, organopolysiloxanes modified with both polyoxyalkylene and alkyl groups, alkanolamides, sugar ethers and sugar amides.

Examples of a usable amphoteric surfactant include betaine, aminocarboxylates and imdazoline derivatives.

These surfactants are preferably modified silicones having a polyoxyalkylene chain in the molecule, and the HLB (hydrophilic lipid balance) of these surfactants is preferably 2–8.

g) Cross-linked Organopolysiloxanes

The cross-linked organopolysiloxanes suitable for the present cosmetic materials are those which cause swelling when they contain a silicone having a low viscosity of from 0.65 to 10.0 cs in a quantity larger than their self weight. Further, it is desirable that the cross-linked structure of those organopolysiloxanes be formed by reaction between hydrogen atoms bonded directly to silicon atoms and a cross-linking agent having at least two vinylic reactive moieties per molecule. Furthermore, it is desirable in the foregoing reaction to use a cross-linking agent containing at least one moiety selected from polyoxyalkylene, alkyl, alkenyl, aryl and fluoroalkyl moieties.

h) Silicone Resins, Such as Acryl/silicone Graft or Block Copolymers and Silicone Lattice Compounds It is preferred that the silicone resins of this invention are acryl silicones. It is moreover preferred that the silicone resins of this invention are acryl silicones containing at least one moiety selected from the group consisting of pyrrolidone, long-chain alkyl, polyoxyalkylene and fluoroalkyl moieties. The other favorable silicone resins are silicone compounds having a lattice structure.

There is no particular limitation on the applications of the makeup of this invention, but examples include skin care products, hairdressing products, antiperspirant, makeup products and ultraviolet defense products. There is also no particular limitation on the form of the product, but it may be applied in liquid, emulsion, cream, solid, paste, gel, powder, laminate, mousse and spray forms.

EXAMPLES

This invention will now be described with reference to specific examples, but the invention should not be construed as being limited to these examples. Further, the term below [%] means [weight %] unless otherwise specified.

Example 1

Synthesis of Silicone Compound 733 weight parts of organohydrogensiloxanes represented by the following average structural formula (7)

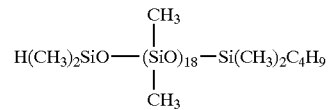

and 1,000 weight parts of isopropyl alcohol were placed in a reaction vessel, and 2 weight parts of a 0.5 weight % isopropyl alcohol solution of chloroplatinic acid was added thereto. The reaction was continued for 6 hours under reflux of the solvent while dripping 70 weight parts of 4-vinyl-1-cyclohexane-1,2-epoxide into the reaction vessel.

Then, the reaction mixture was heated under reduced pressure to distill off excess 4-vinyl-1-cyclohexane-1,2-epoxide and the solvent therefrom, which was replaced by 1000 weight parts of xylene. 165 weight parts of rosin (carboxy equivalent 330 g/mol) was added to the reaction liquor, and the reaction continued for 10 hours under reflux of the solvent. This product was a light brown transparent liquid, viscosity 215 cs (25° C.), specific gravity 1.013 (25° C.).

Example 2

Synthesis of Silicone Compound 768 weight parts of organohydrogensiloxanes represented by the following average structural formula (8):

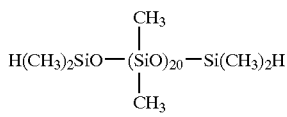

and 1,000 weight parts of isopropyl alcohol were placed in a reaction vessel, and 2 weight parts of a 0.5 weight % isopropyl alcohol solution of chloroplatinic acid was added thereto. The reaction was continued for 6 hours under reflux of the solvent while dripping 40 weight parts of 4-vinyl-1-cyclohexane-1,2-epoxide into the reaction vessel. Then, the reaction mixture was heated under reduced pressure to distill off excess 4-vinyl-1-cyclohexane-1,2-epoxide and the solvent therefrom, which was replaced by 1000 weight parts of xylene. 330 weight parts of rosin (carboxy equivalent 330 g/mol) was added to the reaction liquor, and the reaction continued for 10 hours under reflux of the solvent. This product was a light brown transparent liquid, viscosity 600 cs (25° C.), specific gravity 0.987 (25° C.).

Example 3

Synthesis of Silicone Compound 300 weight parts of organohydrogensiloxanes represented by the following average structural formula (9):

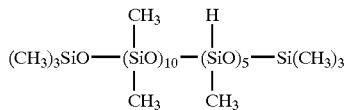

and 1,000 weight parts of isopropyl alcohol were placed in a reaction vessel, and 2 weight parts of a 0.5 weight % isopropyl alcohol solution of chloroplatinic acid was added thereto. The reaction was continued for 6 hours under reflux of the solvent while dripping 70 weight parts of 4-vinyl-1-cyclohexane-1,2-epoxide into the reaction vessel.

Then, the reaction mixture was heated under reduced pressure to distill off excess 4-vinyl-1-cyclohexane-1,2-epoxide and the solvent therefrom, which was replaced by xylene. 413 weight parts of rosin (carboxy equivalent 330 g/mol) was added to the reaction liquor, and the reaction continued for 10 hours under reflux of the solvent. After distilling the reaction liquor under reduced pressure, a viscous, light brown transparent solid was obtained.

Example 4

Synthesis of Silicone Compound 300 weight parts of organohydrogensiloxanes represented by the average structural formula (9) and 1,000 weight parts of toluene were placed in a reaction vessel, and 2 weight parts of a 0.5 weight % toluene solution of chloroplatinic acid was added. The reaction was continued for 6 hours under reflux of the solvent while dripping 360 weight parts of organopolysiloxane represented by the average structural formula (10):

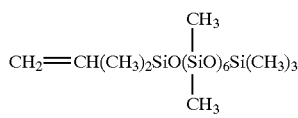

and was continued for a further 6 hours under reflux of the solvent while dripping 105 weight parts of 4-vinyl-1-cyclohexane-1,2-epoxide into the reaction vessel.

Then, the reaction mixture was heated under reduced pressure to distill off excess 4-vinyl-1-cyclohexane-1,2-epoxide and the solvent therefrom, which was replaced by xylene. 240 weight parts of rosin (carboxy equivalent 320 g/mol) was added to the reaction liquor, and the reaction continued for 16 hours under reflux of the solvent. The reaction liquor was distilled off under reduced pressure to obtain the product. This product was a light brown transparent liquid, viscosity 575 cs (25° C.), specific gravity 0.984 (25° C.).

An eyeliner was manufactured using the following ingredients in accordance with the process described below:

| Ingredient | Ratio (weight %) |
| --- | --- |
| (1) Beeswax | 5.0 |
| (2) Cetyl alcohol | 0.4 |
| (3) Stearic acid | 1.0 |
| (4) Silicone compound obtained in Example 3 | 2.0 |
| (5) Sesquioleic acid sorbitan | 0.5 |
| (6) Monooleic acid polyoxyethylene sorbitan | 0.9 |
| (7) Lecitin | 0.1 |
| (8) Black iron oxide | 11.0 |
| (9) Titanium oxide | 0.5 |
| (10) Kaolin | 0.5 |
| (11) 1,3-butylene glycol | 6.5 |
| (12) Antiseptics | 0.2 |
| (13) Purified water | Remainder |
| (14) Silicic acid anhydride | 0.6 |
| (15) Alkali visocity-increasing polymethacrylic acid polymer emulsion* | 2.0 |
| (16) Triethanolamine | 1.1 |
| (17) Silicone acryl emulsion** | 12.0 |

*: Loam & Haas - Lohagid SD-15
*: Shin-Etsu Chemical Co., X-52-2104

Manufacturing Method

Process 1: Components (1)–(10) are heated and homogenized in a roll mill.

Process 2: Components (11)–(16) are mixed.

Process 3: The product of step 1 is heated to 80° C., then the product of step 2 heated to 80° C. is poured in and emulsified.

Process 4: After cooling the product of process 3, component (17) is added to this.

The obtained eyeliner had good adhesive strength and was an excellent eyeliner for makeup.

Embodiment 6

(Manufacture of Lip Cream)

A lip cream was manufactured using the following ingredients in accordance with the process described below:

| Ingredient | Ratio (weight %) |
| --- | --- |
| 1) Polyethylene wax | 4.0 |
| 2) Silicone compound obtained in Example 2 | 8.0 |
| 3) Vaseline | 37.0 |
| 4) Starch fatty acid ester | 7.0 |
| 5) Glycerine fatty acid ester | 40.0 |

13

-continued

| Ingredient | Ratio (weight %) |
| --- | --- |
| 6) Partially cross-linked dimethylpolysiloxane* | 3.0 |
| 7) Hydrophilic spherical silicic acid anhydride** | 1.0 |

*: Shin-Etsu Chemical Co., Inc. -- KSG-16
**: Aerosil 300 (Japan Aerosil Inc.)

Manufacturing Method

The above components were dissolved and dispersed to melt fill a resin dish, and a lip cream was obtained.

The obtained lip cream was a lip cream which was excellent in adhesive strength to the lips, and had emollient properties.

Embodiment 7
(Manufacture of Mascara (Waterproof Types))

Mascara (waterproof type) was manufactured using the following ingredients in accordance with the process described below.

| Ingredient | Ratio (weight %) |
| --- | --- |
| 1. Carnauba wax | 5.0 |
| 2. Micro crystalline wax | 4.0 |
| 3. Silicone resin (MQ resin) | 3.0 |
| 4. Silicone compound obtained in Example 1 | 10.0 |
| 5. Dextrin fatty acid ester | 5.0 |
| 6. Denatured clay mineral | 2.0 |
| 7. Propylene carbonate | 0.6 |
| 8. Silicic acid anhydride | 1.0 |
| 9. Pigment | Suitable amount |
| 10. Light liquid paraffin | Remainder |

Manufacturing Method

Components 1–10 were dissolved by heating, and mixed and dispersed with three rollers to obtain a mascara.

The stability of the obtained mascara was good, it had smooth spreadability, and an excellent feel.

Embodiment 8
(Manufacture of Mascara (W/O type))

Mascara (W/O type) was manufactured using the following ingredients in accordance with the process described below.

| ingredient | Ratio (weight %) |
| --- | --- |
| 1. Carnauba wax | 4.0 |
| 2. Beeswax | 4.0 |
| 3. Silicone compound obtained in Example 4 | 2.0 |
| 4. Behenyl alcohol | 1.5 |
| 5. Acryl silicone* | 3.0 |
| 6. Cane sugar fatty acid ester | 1.5 |
| 7. Sesquioleic acid sorbitan | 2.0 |
| 8. Monooleic polyoxyethylene sorbitan (20E.O.) | 1.0 |
| 9. Surface-treated single crystal titanium oxide | 2.0 |
| 10. Perfluoroalkyl group-containing ester processed black iron oxide | 8.0 |
| 11. Mica | 6.0 |
| 12. Purified water | Remainder |
| 13. Sodium hydroxide | 0.5 |
| 14. 1,3-butylene glycol | 8.0 |
| 15. Antiseptics | Suitable Quantity |
| 16. Polyacrylic acid alkyl water dispersion | 30.0 |
| 17. Nylon terminals | 4.0 |
| 18. Cosmetics components | Suitable Quantity |
| 19. Perfume | Suitable Quantity |

*: Shin-Etsu Chemical Co., Inc -- KP-545

14

Manufacturing Method

A: Components 1–4 are heat fused at 100° C., then components 5–7 are added and dissolved. Components 8–10 are added, and thoroughly mixed to disperse the powders at 75° C.

B: Components 11–17 are heat fused at 75° C.,

C: B is added to A to make an emulsion. This is then degassed, cooled, and component 18 is added to obtain the mascara.

The obtained mascara had good color, adhesive strength to eyelashes, and was an excellent mascara for long-term makeup.

Embodiment 9
(Manufacture of Emulsion Type Foundation)

The emulsion type foundation was manufactured using the following ingredients in accordance with the process described below.

| Ingredient | Ratio (weight %) |
| --- | --- |
| Oil phase | |
| (1) Octamethylcylotetrasiloxane | 10.0 |
| (2) Siliconated cellulose | 2.0 |
| (3) Silicone compound obtained in Example 4 | 5.0 |
| (4) Di-isooctanoic acid neo pentyl glycol | 5.0 |
| (5) Squalane | 2.5 |
| (6Tri-isooctanoic acid glycerol | 2.0 |
| Powder fraction | |
| (7) Siliconized talc | 7.0 |
| (8) Siliconized titanium dioxide | 12.0 |
| (9) Siliconized silicic acid anhydride | 2.0 |
| (10) Silicone powder* | 4.0 |
| (11) Siliconized color pigment | 2.0 |
| Aqueous phase | |
| (12) 1,3-butylene glycol | 10.0 |
| (13) Ethanol | 7.0 |
| (14) Purified water | Remainder |

*: Shin-Etsu Chemical Co., Inc. -- KSP-100

Manufacturing Method

After stirring the aqueous phase, the powder fraction was added and processed in a homomixer. The oil phase which had been dissolved was added, processed in the homomixer, and cooled to give a foundation.

The obtained emulsion type foundation was excellent in adhesive strength, and was excellent in durability of the makeup effect.

Advantages of the Invention

The silicone compound of this invention can be synthesized simply. As an acid catalyst is not needed, safety is also high and it is suitable for blending with makeup. The makeup with which this silicone compound is blended does not have oiliness, is excellent in an adhesive strength, has excellent makeup retention, and also has very good stability in that is unaffected by temperature and time.

What is claimed is:

1. A makeup composition comprising a) 0.1 to 99.5 weight % of a silicone compound of formula (1):

$$R^1{}_a R^2{}_b SiO_{(4-a-b)/2} \qquad (1)$$

wherein $R^1$ is alkyl, aryl, aralkyl, fluorine-substituted alkyl or organopolysiloxanylsilyl of 1–30 carbon atoms, $R^2$ is a carboxylate residue of formula (2):

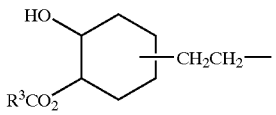
(2)

$R^3$ is a saturated or unsaturated hydrocarbon group having 2–30 carbon atoms, a is 1.0–2.5, and b is 0.001–1.5, and b) 0.5 to 99.9 weight % of an oil.

2. A makeup composition of claim 1, wherein $R^3$ is a tricyclic dipertene carboxylic acid residue.

3. A makeup composition of claim 1, wherein at least part of $R^1$ is represented by formula (3):

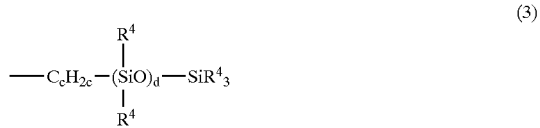
(3)

wherein $R^4$ is, each independently, alkyl, aryl, aralkyl, fluorine-substituted alkyl or hydroxyl of 1–30 carbon atoms, c is 1–5, and d is 0–500.

4. A makeup composition of claim 1, further comprising c) 50 weight % or less of a compound having one or more alcoholic hydroxyl groups in its molecular structure.

5. A makeup composition of claim 4, further comprising d) 99.0 weight % or less of water.

6. A makeup composition of claim 5, further comprising e) a powder, a coloring agent, or both a powder and a coloring agent.

7. A makeup composition of claim 5, further comprising f) a surfactant.

8. A makeup composition of claim 5, further comprising g) a cross-linked organopolysiloxane.

9. A makeup composition of claim 5, further comprising h) a silicone resin.

10. A skin care composition comprising a makeup composition of claim 5.

11. A hairdressing composition comprising a makeup composition of claim 5.

12. An antiperspirant composition comprising a makeup composition of claim 5.

13. A makeup product, comprising a makeup composition of claim 5.

14. An ultraviolet defense composition comprising a makeup composition of claim 5.

15. A skin care composition of claim 10, which is a liquid, emulsion, cream, solid, paste, gel, powder, laminate, mousse or spray.

16. A hairdressing composition of claim 11, which is a liquid, emulsion, cream, solid, paste, gel, powder, laminate, mousse or spray.

17. An antiperspirant of claim 12, which is a liquid, emulsion, cream, solid, paste, gel, powder, laminate, mousse or spray.

18. An makeup product of claim 13, which is a liquid, emulsion, cream, solid, paste, gel, powder, laminate, mousse or spray.

19. An ultraviolet defense composition of claim 14, which is a liquid, emulsion, cream, solid, paste, gel, powder, laminate, mousse or spray.

20. A makeup composition of claim 3, wherein $R^3$ is a tricyclic dipertene carboxylic acid residue.

21. A makeup composition of claim 1, wherein a is 1.2–2.3.

22. A makeup composition of claim 1, wherein b is 0.05–1.0.

23. A makeup composition of claim 1, wherein at least 80% of $R^1$ are methyl groups.

24. A makeup composition of claim 3, wherein c is 2.

25. A makeup composition of claim 3, wherein d is 1–100.

26. A makeup composition of claim 1, wherein $R^3$ is a resin acid or carboxylic acid residue.

27. A makeup composition of claim 1, wherein $R^3$ is tricyclic dipertene carboxylic acid, undecylenic acid, stearic acid or erucic acid.

28. A makeup composition of claim 1, wherein $R^3$ is tricyclic dipertene carboxylic acid.

29. A makeup composition of claim 1, wherein $R^3$ is resin residue of rosin or hydrated rosin.

30. A makeup composition of claim 1, having a weight average molecular weight of 500–200,000.

31. A makeup composition of claim 1, having a weight average molecular weight of 1,000–100,000.

* * * * *